United States Patent
Jayasundera et al.

(10) Patent No.: US 9,898,818 B2
(45) Date of Patent: Feb. 20, 2018

(54) AUTOMATED MEASUREMENT OF CHANGES IN RETINAL, RETINAL PIGMENT EPITHELIAL, OR CHOROIDAL DISEASE

(71) Applicant: THE REGENTS OF THE UNIVERSITY OF MICHIGAN, Ann Arbor, MI (US)

(72) Inventors: Kanishka T. Jayasundera, Ann Arbor, MI (US); Christopher R. Ranella, Macomb, MI (US); Daniel L. Albertus, Ann Arbor, MI (US); Nathan T. Patel, Ann Arbor, MI (US); Victor M. Elner, Ann Arbor, MI (US); Matthew K. Johnson-Roberson, Chestnut Hill, MA (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 262 days.

(21) Appl. No.: 14/341,625

(22) Filed: Jul. 25, 2014

(65) Prior Publication Data
US 2015/0029464 A1  Jan. 29, 2015

Related U.S. Application Data

(60) Provisional application No. 61/858,915, filed on Jul. 26, 2013.

(51) Int. Cl.
*A61B 3/12* (2006.01)
*G06T 7/00* (2017.01)
*G06T 7/254* (2017.01)

(52) U.S. Cl.
CPC .............. *G06T 7/0016* (2013.01); *A61B 3/12* (2013.01); *A61B 3/1241* (2013.01); *G06T 7/254* (2017.01);
(Continued)

(58) Field of Classification Search
CPC ....................................................... A61B 3/12
(Continued)

(56) References Cited

U.S. PATENT DOCUMENTS

| | | | | |
|---|---|---|---|---|
| 5,220,360 A | * | 6/1993 | Verdooner | A61B 3/12 351/212 |
| 6,104,828 A | * | 8/2000 | Shioiri | A61B 3/0058 351/206 |

(Continued)

FOREIGN PATENT DOCUMENTS

WO  WO-2009148067 A1  12/2009

OTHER PUBLICATIONS

Hu, ZhiHong et al.. "Multimodal Retinal Vessel Segmentation from Spectral-Domain Optical Coherence Tomography and Fundus Photography." IEEE Trans Med Imaging 31.10 (2012): 1-28. Print.*

(Continued)

*Primary Examiner* — Zachary Wilkes
(74) *Attorney, Agent, or Firm* — Marshall, Gerstein & Borun LLP; Randall G. Rueth

(57) ABSTRACT

A method for automatically measuring changes in retinal, retinal pigment epithelial, or choroidal disease includes retrieving a set of images of a fundus and selecting a plurality of images from the set of images. The plurality of images are co-registered and pre-processed such that the quality, contrast, and gain of each of the plurality of images is made similar. Then, a comparison is made between the plurality of images to determine a change in retinal, retinal pigment epithelial, or choroidal disease, wherein the change in retinal, retinal pigment epithelial, or choroidal disease is determined based on various disease metrics. Finally, an indication of the change in retinal, retinal pigment epithelial, or choroidal disease is generated for display to a user on a computing device.

21 Claims, 9 Drawing Sheets

(52) U.S. Cl.
CPC ............ G06T 2207/10064 (2013.01); G06T 2207/30041 (2013.01); G06T 2207/30101 (2013.01)

(58) Field of Classification Search
USPC .................................................. 351/246, 206
See application file for complete search history.

(56) References Cited

U.S. PATENT DOCUMENTS

| | | | |
|---|---|---|---|
| 6,698,885 | B2 | 3/2004 | Berger et al. |
| 7,147,329 | B2 | 12/2006 | Berger et al. |
| 7,283,653 | B2 | 10/2007 | Zahlmann et al. |
| 7,474,775 | B2 | 1/2009 | Abramoff et al. |
| 7,488,071 | B2 | 2/2009 | Ogawa et al. |
| 7,512,436 | B2 | 3/2009 | Petty et al. |
| 7,568,800 | B2 | 8/2009 | Mihashi et al. |
| 7,583,827 | B2 | 9/2009 | Hansen et al. |
| 7,856,135 | B1 | 12/2010 | Bernardes |
| 8,041,091 | B2 * | 10/2011 | de Oliveira e Ramos ........... A61B 3/0041 351/206 |
| 2005/0094099 | A1 | 5/2005 | Newman et al. |
| 2005/0171974 | A1 | 8/2005 | Doering |
| 2007/0002275 | A1 | 1/2007 | Yan et al. |
| 2007/0188705 | A1 | 8/2007 | Tajima et al. |
| 2008/0100612 | A1 | 5/2008 | Dastmalchi et al. |
| 2009/0143685 | A1 | 6/2009 | Elner et al. |
| 2010/0302507 | A1 | 12/2010 | Desgroseilliers et al. |
| 2011/0058718 | A1 | 3/2011 | Nakajima et al. |
| 2012/0237096 | A1 | 9/2012 | Tobin et al. |
| 2012/0300998 | A1 | 11/2012 | Ioudovski et al. |

OTHER PUBLICATIONS

Foracchia, Marco et al.. "Luminosity and Contrast Normalization in Retinal Images." Medical Image Analysis 9.3 (2005): pp. 179-190. Print.*

Kexin Deng, Jie Tian, Jian Zheng, Xing Zhang, Xiaoqian Dai, and Min Xu, "Retinal Fundus Image Registration via Vascular Structure Graph Matching," International Journal of Biomedical Imaging, vol. 2010, Article ID 906067, 13 pages, 2010. doi:10.1155/2010/906067.*

A randomized, placebo-controlled, clinical trial of high-dose supplementation with vitamins C and E and beta carotene for age-related cataract and vision loss: AREDS report No. 9. Arch Ophthalmol. Oct 2001;119(10):1439-1452.

Delori F, Greenberg JP, Woods RL, et al. Quantitative measurements of autofluorescence with the scanning laser ophthalmoscope. Invest Ophthalmol Vis Sci. 2011;52(13):9379-9390.

Davis MD, Gangnon RE, Lee LY, et al. The Age-Related Eye Disease Study severity scale for age-related macular degeneration: AREDS Report No. 17. Arch Ophthalmol. Nov. 2005;123(11):1484-1498.

Jager RD, Mieler WF, Miller JW. Age-related macular degeneration. N Engl J Med. Jun. 12, 2008;358(24):2606-2617.

Gobel AP, Fleckenstein M, Schmitz-Valckenberg S, Brinkmann CK, Holz FG. Imaging geographic atrophy in age-related macular degeneration. Ophthalmologica. 2011;226(4):182-190.

Sohrab MA, Smith RT, Fawzi AA. Imaging characteristics of dry age-related macular degeneration. Semin Ophthalmol. May 2011;26(3):156-166.

Gess AJ, Fung AE, Rodriguez JG. Imaging in neovascular age-related macular degeneration. Semin Ophthalmol. May 2011;26(3):225-233.

Schmitz-Valckenberg S, Holz FG, Bird AC, Spaide RF. Fundus autofluorescence imaging: review and perspectives. Retina. Mar. 2008;28(3):385-409.

Delori FC, Fleckner MR, Goger DG, Weiter JJ, Dorey CK. Autofluorescence distribution associated with drusen in age-related macular degeneration. Invest Ophthalmol Vis Sci. Feb. 2000;41(2):496-504.

Holz FG, Bellman C, Staudt S, Schutt F, Volcker HE. Fundus autofluorescence and development of geographic atrophy in age-related macular degeneration. Invest Ophthalmol Vis Sci. Apr. 2001;42(5)1051-1056.

Einbock W, Moessner A, Schnurrbusch UE, Holz FG, Wolf S. Changes in fundus autofluorescence in patients with age-related maculopathy. Correlation to visual function: a prospective study. Graefes Arch Clin Exp Ophthalmol. Apr. 2005;243(4):300-305.

Bressler SB, Bressler NM, Seddon JM, Gragoudas ES, Jacobson LP. Interobserver and intraobserver reliability in the clinical classification of drusen. Retina. 1988;8(2):102-108.

Sunness JS, Bressler NM, Tian Y, Alexander J, Applegate CA. Measuring geographic atrophy in advanced age-related macular degeneration. Invest Ophthalmol Vis Sci. Jul. 1999;40(8)1761-1769.

Scholl HP, Peto T, Dandekar S, et al. Inter- and intra-observer variability in grading lesions of age-related maculopathy and macular degeneration. Graefes Arch Clin Exp Ophthalmol. Jan. 2003;241(1):39-47.

Smith RT, Koniarek JP, Chan J, Nagasaki T, Sparrow JR, Langton K. Autofluorescence characteristics of normal foveas and reconstruction of foveal autofluorescence from limited data subsets. Invest Ophthalmol Vis Sci. Aug. 2005;46(8):2940-2946.

Smith RT, Nagasaki T, Sparrow JR, Barbazetto I, Koniarek JP, Bickmann LJ. Photographic patterns in macular images: representation by a mathematical model. J Biomed Opt. Jan.-Feb. 2004;9(1):162-172.

Hwang JC, Chan JW, Chang S, Smith RT. Predictive value of fundus autofluorescence for development of geographic atrophy in age-related macular degeneration. Invest Ophthalmol Vis Sci. Jun. 2006;47(6):2655-2661.

Smith RT, Chan JK, Busuoic M, Sivagnanavel V, Bird AC, Chong NV. Autofluorescence characteristics of early, atrophic, and high-risk fellow eyes in age-related macular degeneration. Invest Ophthalmol Vis Sci. Dec. 2006;47(12):5495-5504.

Smith RT, Sohrab MA, Pumariega N, et al. Dynamic soft drusen remodelling in age-related macular degeneration. Br J Ophthalmol. Dec. 2010;94(12):1618-1623.

Bearelly S, Cousins SW. Fundus autofluorescence imaging in age-related macular degeneration and geographic atrophy. Adv Exp Med Biol. 2010;664:395-402.

Bearelly S, Khanifar AA, Lederer DE, et al. Use of fundus autofluorescence images to predict geographic atrophy progression. Retina. Jan. 2011;31(1):81-86.

Karadimas P, Bouzas EA. Fundus autofluorescence imaging in serous and drusenoid pigment epithelial detachments associated with age-related macular degeneration. Am J Ophthalmol. Dec. 2005;140(6):1163-1165.

Dimitrov PN, Guymer RH, Zele AJ, Anderson AJ, Vingrys AJ. Measuring rod and cone dynamics in age-related maculopathy. Invest Ophthalmol Vis Sci. Jan. 2008;49(1):55-65.

Dimitrov PN, Robman LD, Varsamidis M, et al. Visual function tests as potential biomarkers in age-related macular degeneration. Invest Ophthalmol Vis Sci. 2011;52(13):9457-9469.

Querques L, Querques G, Forte R, Souied EH. Microperimetric Correlations of Autofluorescence and Optical Coherence Tomography Imaging in Dry Age-Related Macular Degeneration. Am J Ophthalmol. Feb. 7, 2012.

The Age-Related Eye Disease Study system for classifying age-related macular degeneration from stereoscopic color fundus photographs: the Age-Related Eye Disease Study Report No. 6. Am J Ophthalmol. Nov. 2001;132(5):668-681.

Nixon DR. Preoperative cataract grading by Scheimpflug imaging and effect on operative fluidics and phacoemulsification energy. J Cataract Refract Surg. Feb. 2010;36(2):242-246.

Chylack LT, Jr., Wolfe JK, Singer DM, et al. The Lens Opacities Classification System III. The Longitudinal Study of Cataract Study Group. Arch Ophthalmol. Jun. 1993;111(6):831-836.

Richter-Mueksch S, Sacu S, Weingessel B, Vecsei-Marlovits VP, Schmidt-Erfurth U. The influence of cortical, nuclear, subcortical posterior, and mixed cataract on the results of microperimetry. Eye (Lond). Oct. 2011;25(10):1317-1321.

(56) References Cited

OTHER PUBLICATIONS

Rafael C. Gonzalez, Richard E. Woods, and Steven L. Eddins. 2003. *Digital Image Processing Using MATLAB*. Prentice-Hall, Inc., Upper Saddle River, NJ, USA.

RetmarkerAMD Research. (2010). Retrieved Jun. 18, 2013 from Critical Health, SA Website: <http://www.retmarker.com/docs/RetmarkerAMDResearch.pdf>.

RetmarkerC Automatic Detection of Retinal Changes. (n.d.). Retrieved Jun. 18, 2013 from Critical Health, SA Website: <httb://www.retmarker.com/docs/RetmarkerC.pdf>.

RetmarkerDR Biomarker for Diabetic Retinopathy Progression. (2009). Retrieved Jun. 18, 2013 from Critical Health, SA, Website: <http://www.retmarker.com/docs/RetmarkerDR.pdf>.

Schachar IH, Zahid S, Comer GM, Stem M, Schachar AG, Saxe SJ, Gardner TW, Elner VM, Jayasundera T. Quantification of Fundus Autofluorescence to Detect Disease Severity in Nonexudative Age-Related Macular Degeneration. *Jama Ophthalmol*, Jun. 20, 2013, E1-E7.

International Search Report and Written Opinion for corresponding International Patent Application No. PCT/US2014/048222, dated Nov. 13, 2014.

\* cited by examiner

AUTOMATED MEASUREMENT OF CHANGES IN RETINAL, RETINAL PIGMENT EPITHELIAL, OR CHOROIDAL DISEASE

CROSS-REFERENCE TO RELATED APPLICATIONS

This application claims priority to U.S. Provisional Patent Application No. 61/858,915, filed on Jul. 26, 2013, and titled "AUTOMATED MEASUREMENT OF CHANGES IN RETINAL, RETINAL PIGMENT EPITHELIAL, OR CHOROIDAL DISEASE," the entire disclosure of which is hereby expressly incorporated by reference herein.

TECHNICAL FIELD

The present disclosure generally relates to methods for the presentation and analysis of images of the retina and, more particularly, to an automated method for measuring changes in retinal, retinal pigment epithelial, or choroidal disease.

BACKGROUND

The fundus of the human eye is the interior surface of the eye, opposite the lens, and includes the retina, optic disc, retinal pigment epithelium (RPE), and the choroid. The retina is a thin layer of neural tissue at the back of the eye that transforms light into electrical signals for the brain, and the choroid is a vascular layer of the eye under the retina. The retina can be divided into two distinct regions related to their visual function. These regions are the macula, where the majority of photoreceptor cells (responsible for central, high acuity color vision) lie, and the periphery, which includes everything outside the macula. The macula includes a region known as the fovea, which is responsible for our high acuity vision.

To observe and monitor the structure of the retina or choroid, physicians currently rely on various medical imaging techniques, such as fluorescein angiography (FA) imaging, indocyanine green (ICG) imaging, and fundus autofluorescence (FAF). FA/ICG allows physicians to observe the accumulation of fluid from retinal or choroidal vessels, the formation of new retinal or choroidal blood vessels, and the loss of perfusion of blood in retinal vessels and choroidal vessels which cause vision loss and retinal dysfunction. The leakage of fluid can be observed as a growing region of hyperfluoresence in time elapsed FA images in areas of the retina or beneath the retina where fluid leaks, formation of new blood vessels will be seen as hyperfluorescent networks of vessels and loss of perfusing blood vessels will be seen as areas of hypofluorescence in FA and ICG imaging.

FAF imaging relies on the inherent fluorescence of proteins and other molecules produced in the retina and RPE. The reflected light from these molecules is captured and transformed into an electrical signal (e.g., an electrical current) to be processed and displayed as a grayscale image of the retina. In such an image, areas exhibiting excessive accumulation of metabolic products (e.g., lipofuscin) appear bright as compared with surrounding tissue, and areas with decreased accumulation appear dark. Further, areas where cells have died completely (e.g., due to a process known as atrophy) appear black. Bright regions can be described as hyperfluorescent, and dark regions can be described as hypofluorescent. Both hyperfluorescent and hypofluorescent regions are disease signatures, or disease markers, that reflect dysfunction in retinal tissue, such as the photoreceptor cells described above.

Current FAF, FA, and ICG techniques rely on a subjective interpretation of disease signatures. Yet, hyperfluorescence and hypofluorescence are sometimes hard to visually distinguish from shadows or changes in FAF, FA, or ICG image acquisition gain and contrast, making subtle changes in disease signatures hard to quantify. As a result, FAF, FA, and ICG assessment has developed into a primarily descriptive, rather than quantifiable, process. Without an objective quantification process, variability in clinical grading can be a barrier to measuring the effectiveness of disease interventions or determining a prognosis to guide treatment.

SUMMARY

In one embodiment, a computer-implemented method for automatically measuring changes in retinal, retinal pigment epithelial, or choroidal disease comprises retrieving, with one or more processors, a set of images of a fundus and selecting, with the one or more processors, a plurality of images from the set of images, wherein the plurality of images includes images of the fundus captured at successive times. Further, the method comprises co-registering, with the one or more processors, the plurality of images, wherein co-registering the plurality of images includes: detecting a plurality of blood vessel locations within each of the plurality of images, correlating the detected plurality of blood vessel locations in one of the plurality of images with a plurality of blood vessel locations in the remaining plurality of images, and transforming the remaining plurality of images such that blood vessel locations in the remaining plurality of images are proximate to the detected plurality of blood vessel locations in the one of the plurality of images. Still further, the method comprises pre-processing, with the one or more processors, the plurality of images such that the quality, contrast, and gain of each of the plurality of images is made similar, performing a comparison, with the one or more processors, of the plurality of images to determine a change in retinal, retinal pigment epithelial, or choroidal disease, wherein the change in retinal, retinal pigment epithelial, or choroidal disease is determined based on various disease metrics, and generating, with the one or more processors, an indication of the change in retinal, retinal pigment epithelial, or choroidal disease to be displayed to a user of a computing device.

In another embodiment, a computer device for automatically measuring changes in retinal, retinal pigment epithelial, or choroidal disease comprises one or more processors and one or more non-transitory memories coupled to the one or more processors, wherein the one or more memories include computer executable instructions stored therein that, when executed by the one or more processors, cause the one or more processors to: retrieve a set of images of a fundus and select a plurality of images from the set of images, wherein the plurality of images includes images of the fundus captured at successive times. Further, the computer executable instructions cause the one or more processors to co-register the plurality of images, wherein co-registering the plurality of images includes: detecting a plurality of blood vessel locations within each of the plurality of images, correlating the detected plurality of blood vessel locations in one of the plurality of images with a plurality of blood vessel locations in the remaining plurality of images, and transforming the remaining plurality of images such that blood vessel locations in the remaining plurality of images are proximate to the detected plurality of blood vessel locations in the one of the plurality of images. Still further, the computer executable instructions cause the one or more processors to pre-process the plurality of images such that the quality, contrast, and gain of each of the plurality of images is made similar, perform a comparison of the plurality of images to determine a change in retinal, retinal pigment epithelial, or choroidal disease, wherein the change in retinal, retinal pigment epithelial, or choroidal disease is determined based on various disease metrics, and generate an indication of the change in retinal, retinal pigment epithelial, or choroidal disease to be displayed to a user of a computing device.

DETAILED DESCRIPTION

Although the following text sets forth a detailed description of numerous different embodiments, it should be understood that the legal scope of the description is defined by the words of the claims set forth at the end of this disclosure. The detailed description is to be construed as exemplary only and does not describe every possible embodiment since describing every possible embodiment would be impractical, if not impossible. Numerous alternative embodiments could be implemented, using either current technology or technology developed after the filing date of this patent, which would still fall within the scope of the claims.

It should also be understood that, unless a term is expressly defined in this patent using the sentence "As used herein, the term '_____' is hereby defined to mean . . ." or a similar sentence, there is no intent to limit the meaning of that term, either expressly or by implication, beyond its plain or ordinary meaning, and such terms should not be interpreted to be limited in scope based on any statement made in any section of this patent (other than the language of the claims). To the extent that any term recited in the claims at the end of this patent is referred to in this patent in a manner consistent with a single meaning, that is done for the sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph.

System Overview

Figure 1:
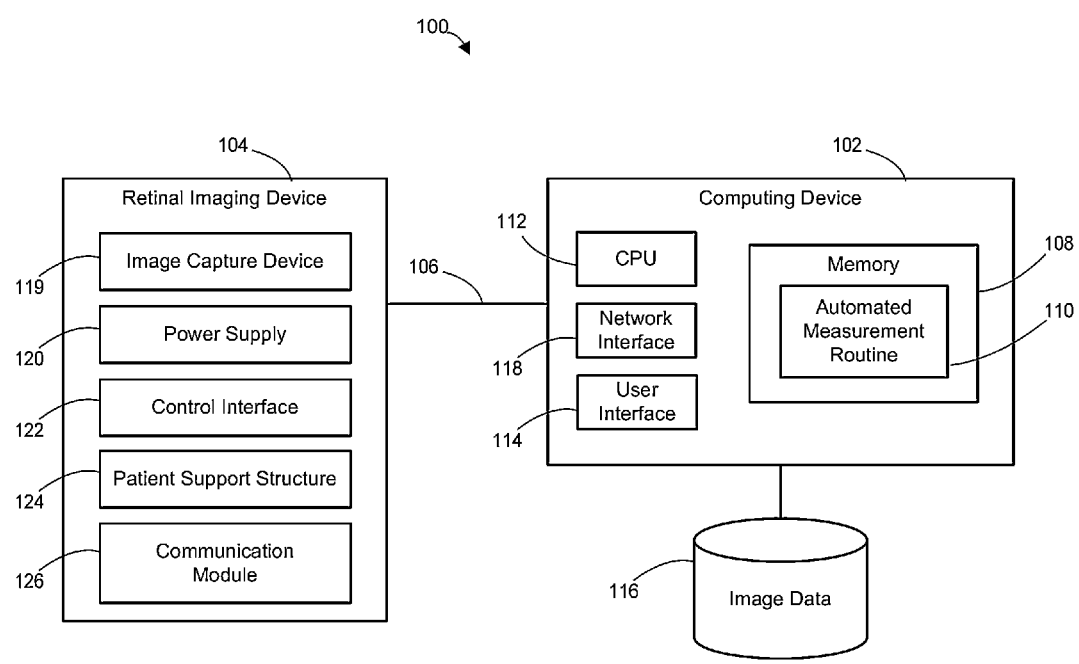
FIG. 1 illustrates an example system in which a computing device can automatically measure changes in retinal, retinal pigment epithelial, or choroidal disease.

FIG. 1 illustrates an example system 100 in which a computing device 102 may automatically measure changes in retinal, retinal pigment epithelial, or choroidal disease by analyzing images of the fundus from a retinal imaging device 104. In some implementations, the computing device 102 and the retinal imaging device 104 may be communicatively connected such that the retinal imaging device 104 may transfer images to the computing device 102 for analysis. For example, the computing device 102 and the retinal imaging device 104 may be operatively connected via a wired connection such as a coaxial cable, optical fiber cable, universal serial bus (USB), or twisted pair cable. Alternatively, the computing device 102 and the retinal imaging device 104 may be connected via any suitable wired or wireless network, such as a wireless local area network (WLAN), for example.

However, a user may transfer images from the retinal imaging device 104 to the computing device 102 via a removable memory device (not shown), in some implementations. For example, a user may download images onto a removable memory device, such as a flash memory card, from the retinal imaging device 104, physically transfer the removable memory device to the computing device 102, and subsequently upload the images from the removable memory device to the computing device 102. Thus, in some implementations, a communicative connection 106 between the computing device 102 and the retinal imaging device 104 is not necessary.

The computing device 102 includes a memory 108 that can include both volatile and nonvolatile memory components and that stores an automated measurement routine 110, in an embodiment. When executed by a CPU 112, the automated measurement routine 110 may receive input from a user of the computing device 102 via user interface 114 (e.g., including a keyboard, mouse, touchscreen, etc.), pre-process images from the retinal imaging device 104, and automatically evaluate changes in retinal, retinal pigment epithelial, or choroidal disease based on the images from the retinal imaging device 104, for example. Further details of a method for automatically evaluating changes in retinal, retinal pigment epithelial, or choroidal disease are discussed with reference to FIG. 2 and FIG. 7.

In some implementations, the computing device 102 or the retinal imaging device 104 may store images (e.g., captured images of retinas), in an image database 116 communicatively connected to the computing device 102. For example, the image database 116 may store images of a patient's fundus over time, thus allowing the computing device 102 to analyze time elapsed imagery of a patient's fundus. In some cases, the image database 116 may be a remote database that is not physically connected to the computing device 102. For example, the image database 116 may be a network accessible database with which the computing device 102 may communicate via a network interface 118.

Although FIG. 1 illustrates the computing device 102 and the image database 116, a system to automatically measure changes in retinal, retinal pigment epithelial, or choroidal disease may include any suitable number of computing devices and databases communicatively coupled to the retinal imaging device 104 and/or utilized to analyze imagery from the retinal imaging device 104. For example, multiple images of a patient's fundus may be stored on multiple databases and analyzed by multiple computing devices, each having one or more processors.

Returning to FIG. 1, the retinal imaging device 104 includes an image capture device 119, a power supply 120, a control interface 122, a patient support structure 124, and a communication module 126. For example, the retinal imaging device may be a non-mydriatic or mydriatic (i.e., making use of dilation) retinal camera, as known in the industry. A patient's head may rest on the patient support structure 124 (e.g., chin rest) and an operator may use the control interface 122 (e.g., including joysticks, buttons, touchscreens, displays, etc.) to control the image capture device (e.g., digital camera) and acquire an image of the patient's retina. Upon acquisition, the image may be transferred to the computing device 102 via the communication module 126 or stored in a local memory (not shown), in an implementation. In some cases, the images may be stored on a removable memory device communicatively attached the retinal imaging device 104, as discussed above.

Image Preparation and Processing

Figure 2:
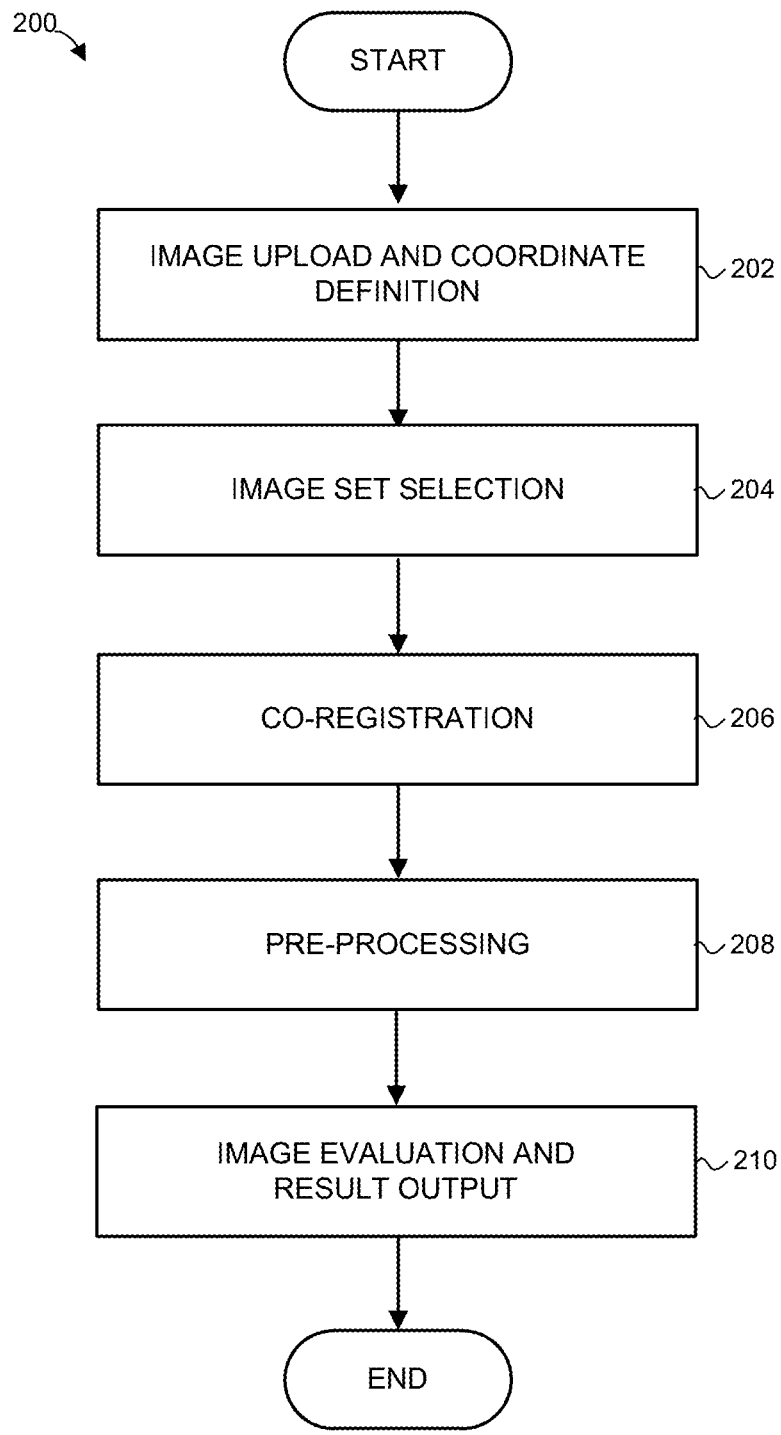
FIG. 2 is a flow diagram of an example method for automatically measuring changes in retinal, retinal pigment epithelial, or choroidal disease which can be implemented by the computing device illustrated in FIG. 1.

FIG. 2 is a flow diagram of an example method 200 for automatically measuring changes in retinal, retinal pigment epithelial, or choroidal disease. The method 200 may be implemented by the computing device 102, for example.

To begin, images of a patient's fundus are uploaded or input to a computing device and coordinates of certain fundus structures are defined (block 202). In an implementation, a user may specify (e.g., via a user interface, such as user interface 114) images corresponding to a patient name, patient identification number (PIN), image capture date, etc. For example, a user may use a graphical user interface (GUI) displayed on the user interface 114 to navigate through directories of the image database 116, specify images from lists or thumbnail views of images (e.g., labeled by patient name and capture date), and transfer (e.g., via a drag and drop operation) images to the computing device 102 for analysis. However, in some implementations, the process of obtaining images of a patient's retina may be automated. For example, a user may need only to enter a patient name or patient identification number (PIN) via a form (e.g., an XML form). The computing device 102 may then automatically query the image database 116 and return to the user images matching the patient name/PIN or sets of images acquired for various sorts of analysis, for example.

A GUI presented to the user may also prompt the user for input related to the location of multiple structures in the eye to be used as landmarks for analysis, in an embodiment. For example, a GUI may prompt the user for coordinates of retinal structures, which, by way of example, may include the fovea and optic disc in a baseline image (e.g., the oldest of the available images). Alternatively, the automated measurement routine 110 may use computer vision techniques to automatically determine the coordinates of retinal structure without user intervention, in an embodiment. For example, machine learning or other suitable algorithms, as known in the industry, may be used to automatically determine the coordinates of the fovea and optic disc in a reference image (e.g., the selected image with the oldest date of capture).

In an implementation, the automated measurement routine 110 may use such coordinates to determine the location of the macula and, thus, the area outside the macula in an image. For example, the region outside the macular may be specified by a ring between the fovea and optic disc of some varying inner and outer radius. However, any suitable estimate of the location of the fovea and optic disc in the oldest image (by visitation date) may be used for this purpose as co-registering of subsequent images using computer determined control points such as vessel bifurcations, a process to be described in detail below, ensures the matching of landmark retinal structures.

After image upload and coordinate definition, a set of images is selected for analysis (block 204). In some implementations, a user may be prompted to manually select images from available patient images. For example, the automated measurement routine may present, via the user interface 114, a thumbnail view of multiple available retinal images corresponding to a patient, and the user may select two or more of these images for analysis. Alternatively, the automated measurement routine 110 may automatically (i.e., without user interaction) choose all available images, a subset of images from a certain time period, or a pre-defined number of most recent images for analysis, in an embodiment. To measure changes in retinal, retinal pigment epithelial, or choroidal disease, the automated measurement routine 110 may require at least two images captured at differing times. Further, in some implementations, the automated measurement routine 110 may remove any color components in the selected images by applying a grayscale filter to the selected images.

Figure 3A:
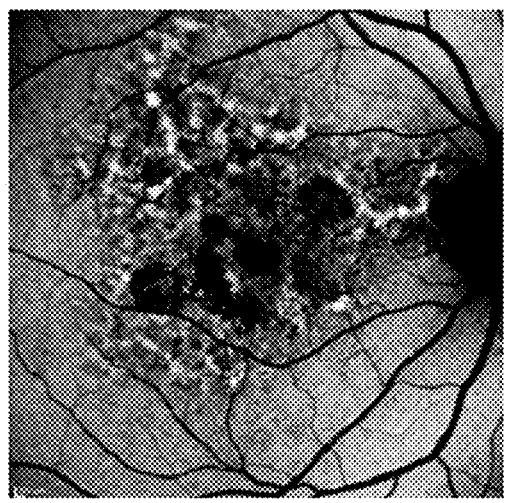
FIGS. 3A and 3B are example images to be analyzed in determining changes in macular disease such as in the method described in FIG. 2.
Figure 3B:
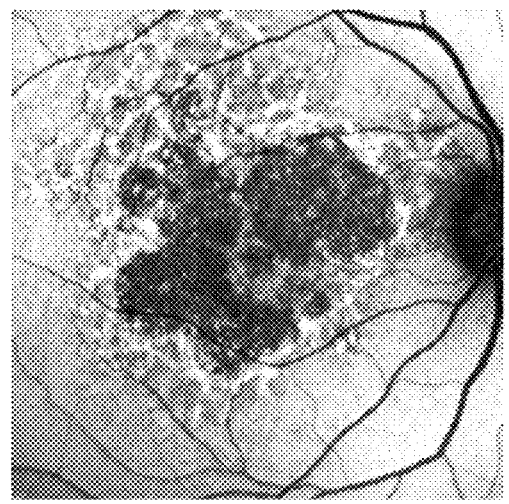
Figure 4A:
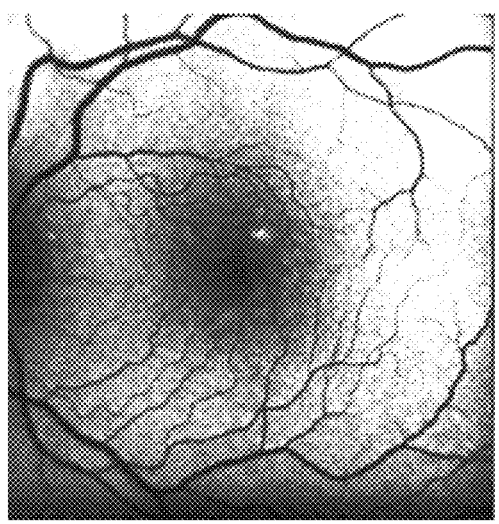
FIGS. 4A-4D are example images processed for blood vessel detection such as in the method described in FIG. 2.
Figure 4B:
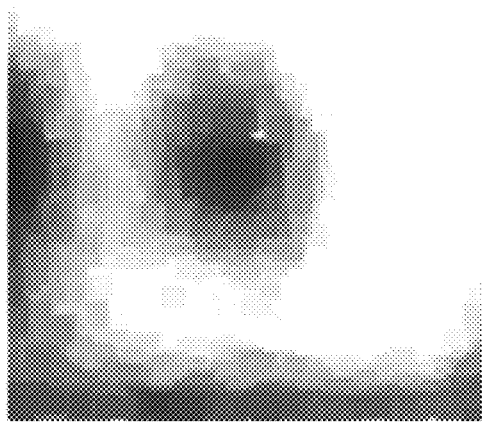
Figure 4C:
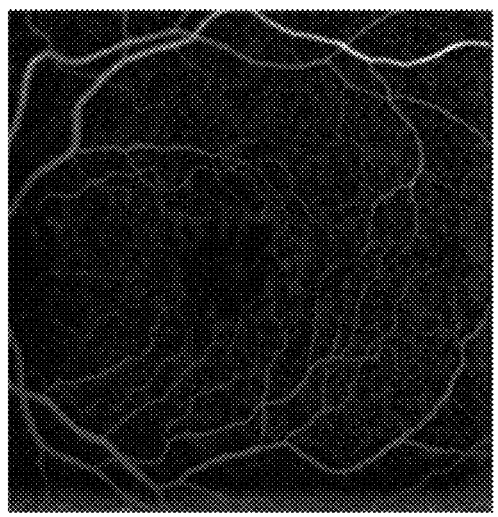
Figure 4D:
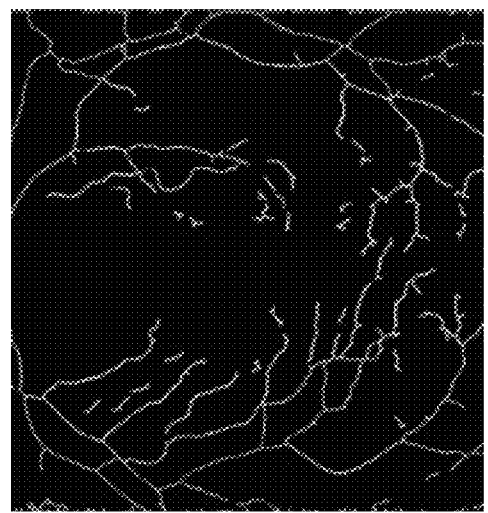

FIGS. 3A and 3B are two example FAF images captured at a first visit to a clinic and a second visit to a clinic, respectively. The two images in FIGS. 3A and 3B may be selected for analysis either manually by a user or automatically by a computer routine, as discussed above. Since the image presented in FIG. 3A was captured before the image presented in FIG. 3B, coordinates of landmark retinal structures may also be identified in FIG. 3A either by user selection (e.g., by clicking on the structures) or automatically via a computer vision technique. Although FIGS. 3A and 3B illustrate FAF images, any suitable images of the retina may be analyzed by the method 200, such as FA and ICG images. Further, any suitable number of images, greater than or equal to two, may be selected for analysis. For example, a user may select three angiogram images, representing early, mid, and late times, for analysis.

Returning to FIG. 2, the selected images are co-registered such that pixels correlate as closely as possible across images (block 206). In this way, retinal or choroidal regions in subsequent images may be accurately compared, and variations due to camera and/or eye movement during image acquisition may be minimized.

In an embodiment, the automated measurement routine 110 utilizes co-registration techniques that account for translational and rotational shifts in the retina or choroid between images and dimensional differences. For example, the automated measurement routine 110 may utilize a registration technique that: (i) detects blood vessel points, (ii) determines the correspondence between vessel points, and (iii) estimates image transformation. By way of example and without limitation, specific techniques are presented below for the steps (i), (ii), and (iii), but any suitable techniques may be implemented to accomplish (i), (ii), and (iii).

(i) For detecting blood vessel points, the automated measurement routine 110 may utilize a Gaussian filter, bottom hat filter, and thresholding technique, in an embodiment (FIGS. 4A-4D are example images generated with some of these techniques). For example, the Gaussian filter may first smooth out noise and then the bottom hat filter may suppress vessels within the image during a "morphological closure" of the image, as known in the industry (see FIG. 4B for an example morphological closuring of FIG. 4A). Subsequently, the automated measurement routine 110 may subtract the Gaussian filtered image and the bottom hat filtered image and use a threshold value to convert the grayscale image to a binary image of zeros (non-vessels) and ones (vessels), for example (see FIG. 4C for an example subtraction of 4A from 4B and see FIG. 4D for an example "skeletonized" version of FIG. 4C generated at least partially by a thresholding process).

Figure 5:
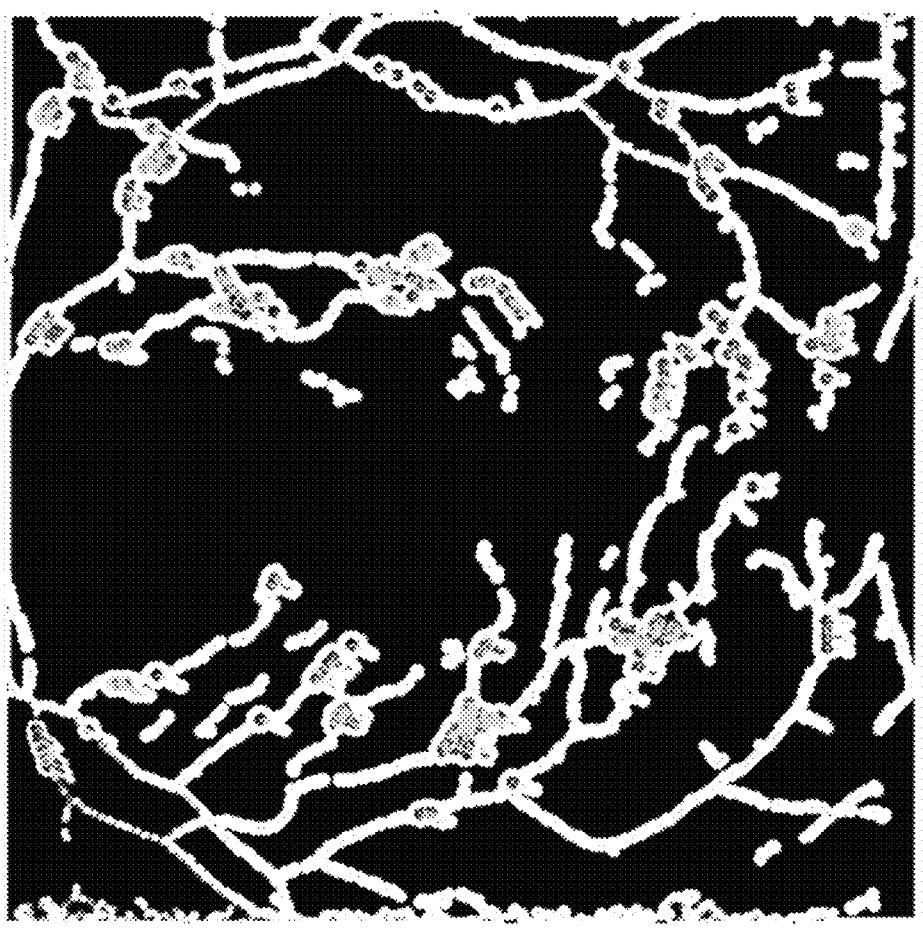
FIG. 5 is an example image with control points and transformation indications for a co-registration process such as in the method described in FIG. 2.

(ii) For determining the correspondence between vessel points (or control points), the automated measurement routine 110 may use cross correlation techniques to determine the degree to which two matrices, which encompass information about each vessel pixel, are correlated, in an embodiment. For example, the cross correlation algorithm may iterate over the possible vessel matches and calculate the normalized similarity between corresponding matrices. The algorithm may then determine the most similar matches between matrices (e.g., the similar vessel points). In some implementations, the algorithm may also segment the image into a number of regions, find the local mode of translation for each region of the image, and statistically eliminate outliers. Further, the algorithm may exclude regions, in particular those with pathological disease characteristics, in an implementation. For example, by ignoring the macula, vessel detection may become more accurate. See FIG. 5 for an example image in which vessel points (represented by circles) are identified and correlated with another image, or baseline image.

(iii) For estimating image transformations, the automated measurement routine 110 may estimate an affine transformation by utilizing a Random Sample Consensus (RANSAC) algorithm. An affine transform allows for a manipulation of an image in the x-offset, y-offset, rotation, and scale while maintaining straight lines in an image. This preserves the features of an image and allows for pixels to be transformed while still maintaining their position relative to each other along with feature information and pixel orientation. The RANSAC algorithm may be highly efficient and allows for a set of matched points (e.g., vessel points) to be transformed to minimize the difference between the original matrix and the transformed matrix, for example. For example, each control point in FIG. 5 has a line indicating the transformation needed to align said control point with the corresponding point in a baseline image.

In certain scenarios, the automated measurement routine 110 may be unable to co-register uploaded or selected images due to the quality of the images. For example, the conditions under which an image was captured may be such that the resulting image is extremely dark or light (over/under exposed), blurry, etc. In such cases, the method 200 may include a step, before co-registration or as part of the co-registration process, that automatically validates images to be appropriate for co-registration and alerts a user if images are not valid for co-registration (i.e., are not able to be co-registered), in an implementation. For example, if images are of poor quality, based on certain image processing metrics, the automated measurement routine 110 may alert the user of this fact and request that other images be provided for analysis. Alternatively, if enough (e.g., more than two) images are available in the selected set of images, the automated measurement routine 110 may delete a poor quality image from the set of images and continue analysis with the remaining images, assuming the remaining of the set of images is of adequate quality for co-registration.

Figure 6A:
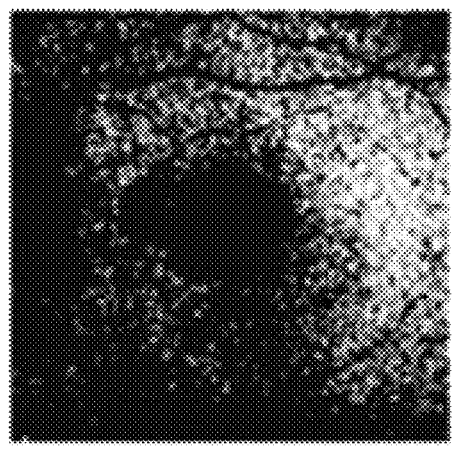
FIGS. 6A and 6B are example images before and after pre-processing such as in the method described in FIG. 2.
Figure 6A:
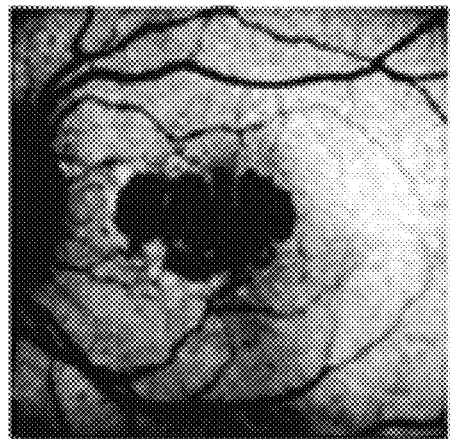
Figure 6B:
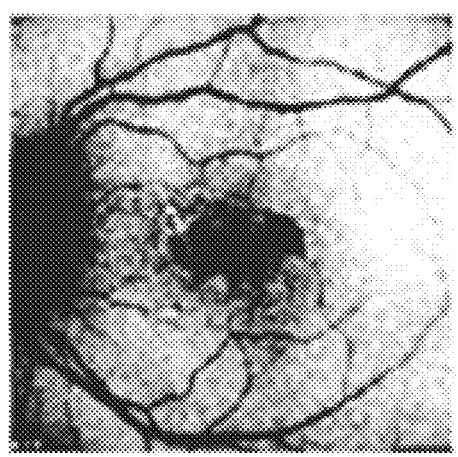
Figure 6B:

Again returning to FIG. 2, selected and co-registered images are pre-processed (block 208). In some implementations, the automated measurement routine 110 uses a number of image processing techniques to ensure the selected images are as similar as possible with respect to quality, contrast, and gain. To illustrate the effects of pre-processing, FIGS. 6A and 6B each include two example images, an image before pre-processing on the left and an image after pre-processing on the right.

As an illustrative example, the automated measurement routine 110 may use a second Gaussian filter to smooth pixel noise and/or account for differences in resolution between selected images during pre-processing. In some cases, the window (or radius) of a second Gaussian filter applied to the images may be proportional to the resolution of one or more images selected for analysis. Thus, the window of the Gaussian filter may be dynamic and automatically account for image resolution differences.

Also, in some implementations, the automated measurement routine 110 may utilize a least squares fitting technique to scale all pixel intensities, such that all images are similar with respect to brightness or intensity. For example, an application of linear regression, with respect to a first image, may result in a coefficient that, when multiplied by all pixel values in a second image, produces a second image satisfying a certain criteria. That certain criteria may declare, for example, that the mean pixel values in concentric rings in the second image are as close as can be achieved, by linear scaling, to the means of corresponding rings in the first image.

Linear regression techniques utilized by the automated measurement routine 110 may only consider concentric rings outside the macula, in some implementations, as this eliminates possible variations between images. The linear regression techniques may assume that a linear relationship accurately models the difference in gain that may be present between images. However, in other embodiments, the automated measurement routine 110 may implement higher order polynomial, or other suitable, fitting to obtain a more accurate relationship between image intensities.

As an alternative example technique for mitigating intensity variations, the automated measurement routine 110 may utilize top hat filtering to suppress background variation, in an embodiment. For example, a top hat filter may standardize background intensity in a manner that preserves objects in the macula but completely eliminates all other variation by smoothing the background to black, for example. Thus, the filtered images are solely characterized by disease markers and non-disease related variation is eliminated, in the embodiment.

In addition to matching intensity, automated measurement routine 110 may also address differences in contrast during pre-processing, in an implementation. For example, to ensure discernible detail is present in each image, the automated measurement routine 110 may perform dynamic gamma scaling. By adding a dynamic range of gamma values, this technique of dynamic gamma scaling may also increase the amount of discernible detail present when the distribution of pixel values in an image lies on one particular side of the contrast spectrum. For example, if an image is uniformly dark, gamma scaling will not only increase the separation in pixel values to provide greater contrast, but gamma scaling will increase the separation in pixel values on the dark end of the spectrum more as compared with values on the light end of the spectrum.

The automated measurement routine 110 may achieve such a dynamic scaling by using the mean of a sampled ring between the fovea and optic disc as a threshold to determine what gamma value should be used, in an implementation. Gamma values less than one correspond to increased contrast stretching in the dark (low) end of the contrast spectrum while values of gamma greater than one correspond to increased contrast stretching in the light (high) end of the spectrum. Therefore, if the mean pixel intensity in a ring between the macula and optic disc is between a range of values on the dark end of the spectrum, the pixels of that image will be gamma scaled with a gamma value greater than one, for example.

In one embodiment, the automated measurement routine 110 may utilize model intensity maps generated from a large composite set of fluorescence images to scaled pixel intensities between images. This model intensity mapping process would eliminate the need for addressing contrast differences because it would allow the pixel intensities of images to be standardized to a model that already incorporates an acceptable amount of contrast between regions/objects, for example. In order to standardize the intensities of specific regions or objects, various computer automated image segmentation techniques, as known in the industry, may segment retinal images into regions based on intrinsic properties such as dark pixel uniformity in areas of atrophy bounded by sharp gradients, in an implementation. For example, property identification and boundary reconstruction algorithms may be coupled with a segmentation process such as quad tree decomposition or watershed segmentation to identify regions consisting solely of extracted object(s). Once such image segmentation is complete, the automated measurement routine 110 may carry out object specific intensity scaling (e.g., histogram matching, object re-coloration), in the implementation.

In another embodiment of pre-processing, image segmentation techniques involving gradient filters (e.g., using either canny or sobel approximations) and at least one instance of image closing, opening, erosion, or dilation may be used to eliminate non-disease related intensity variation and recolor regions of non-perfusion. Further details of such an embodiment are discussed with reference to FIGS. 9A-9D in which regions of non-perfusion are recolored black via masking.

Finally, the selected, co-registered, and pre-processed images are evaluated for changes in retinal, retinal pigment epithelial, or choroidal disease and the results of the evaluation are output to a user (block 210). Once comparable images have been obtained (via blocks 202-210), the method 200 determines regions in each image to evaluate based on the registered locations of the fovea and optic disc, in an implementation. Analysis of these macular windows may involve equally dividing the windows into grid boxes and computing metrics within or between grid boxes, for example. Image evaluation is further discussed with reference to FIG. 7.

In an implementation, the results of image evaluation may be output to a user in a variety of forms. For example, results output may include: colored 3D surface plots of pixel intensity that allow easy user assessment of the relative sizes of disease markers, comparison figures in which progression or regression of disease markers related to hyperfluorescence or hypofluorescence between analyzed images is identified and highlighted, and quantification metrics that represent the total variation due to changes in hyperfluorescence and/or hypofluorescence between analyzed images along with the individual variation of each from a solid gray image. Results may be displayed on the user interface 114, for example (e.g., on a computer monitor, touchsceen, etc.).

In some cases, additional visual outputs may be generated, where the additional visual outputs label specific disease marker. For example, a label of a specific disease marker may indicate that the marker is "progressing" or "regressing" and by what corresponding quantifiable amount. Thus, changes in retinal, retinal pigment epithelial, or choroidal disease may be automatically and objectively quantified and display for a user.

The output of method 200 may be stored in directories (e.g., in image database 116) specific to each set images, directories specified by the user, or directories specific to a test data/event. As such, the method 200 may produce results that facilitate side-by-side analysis of results by means of display screens showing several images corresponding to a single analysis of images or multiple different image analyses.

Image Evaluation

Figure 7:
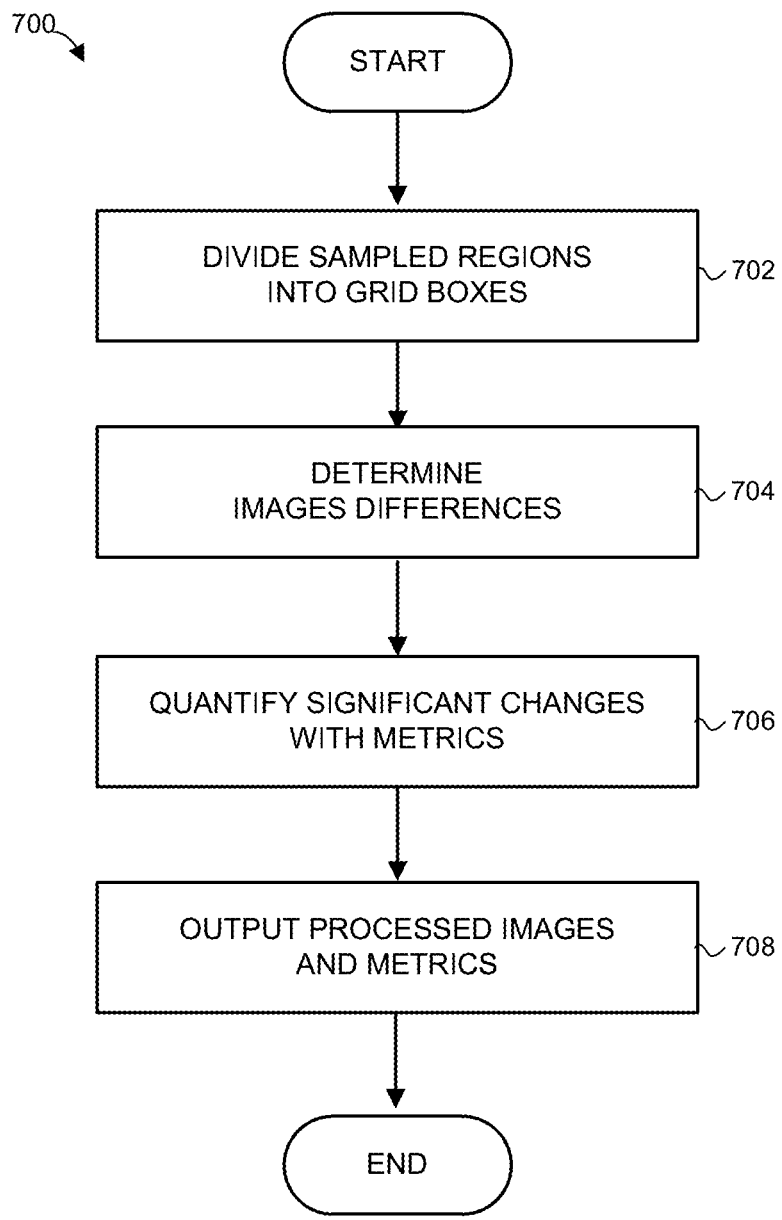
FIG. 7 is a flow diagram of an example method for evaluating changes in retinal, retinal pigment epithelial, or choroidal disease which can be implemented by the computing device illustrated in the system of FIG. 1.

FIG. 7 is a flow diagram of an example method 700 for evaluating images to determine changes in retinal, retinal pigment epithelial, or choroidal disease. The method may be implemented by the computing device 102 and/or as part of block 210 of method 200, for example.

First, sampled regions, or windows, are divided into a set of grid boxes (block 702). The automated measurement routine 110, for example, may determine regions in each image to evaluate based on the registered locations of the fovea and optic disc (e.g., as defined at block 202 of method 200). In some implementations, the automated measurement routine 110 determines rectangular windows around the fovea in each image and scales the images to encompass only the macula. This window determination may be achieved by allowing the windows to run some distance vertically and horizontally, where the specific horizontal and vertical distances are calculated to be a proportion of the distance between the fovea and optic disc, for example.

The sampled regions are then equally divided into grid boxes in order to eliminate differences in image size/resolution, in some implementations. However, any suitable uniform or non-uniform grid of cells may be used to segment or divide each of the sampled windows.

Differences, or changes, between earlier and later images are then determined (block 704). For each window, the automated measurement routine 110 may determine the mean pixel intensity in each one of the grid boxes and store these values in a matrix. By subtracting the matrix obtained from an older image from that of the more recent image, a matrix representing changes between imaging visits is calculated, in an implementation. The automated measurement routine 110 may use thresholds to determine whether a change within a grid box represents an increase or decrease in hyperfluorescence or hypofluorescence, for example.

Changes in retinal images are then quantified using one or more metrics (block 206). For example, the automated measurement routine 110 may calculate the mean of the squared differences between all grid boxes that have changed above the aforementioned thresholds and have, therefore, been determined to have been subject to retinal, retinal pigment epithelial, or choroidal disease progression. Other quantification metrics may include, for example, the mean of squared differences related solely to hyperfluorescence, the mean of squared differences related solely to hypofluorescence, and a mean squared difference between the sampled windows and a solid gray window.

Figure 8:
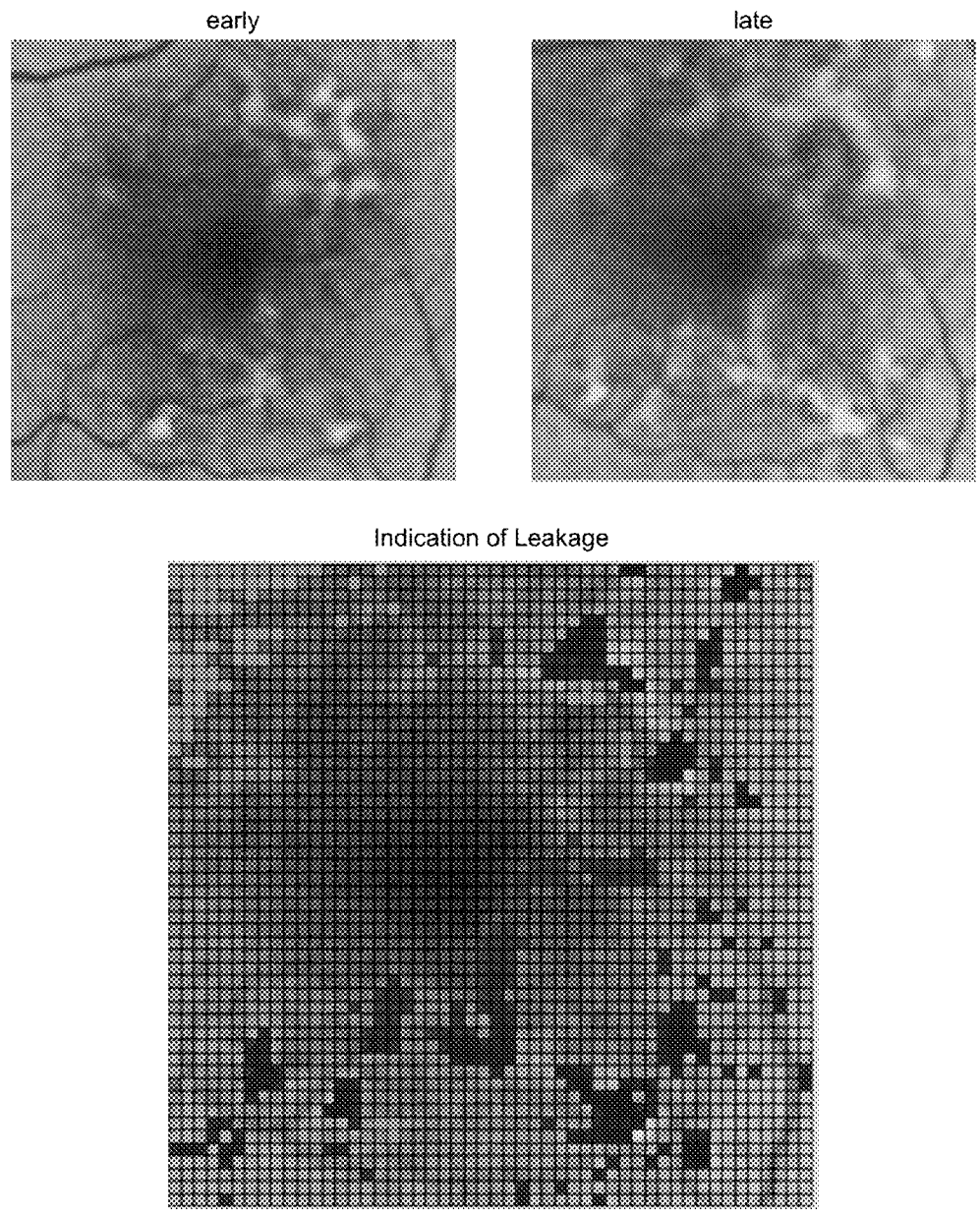
FIG. 8 is an example image of an output of the evaluation of changes in an FA image of diabetic macular disease such as in the method described in FIG. 7.

After computing the metrics, the metrics and/or visualization of the metrics are output to a user (block 208). For example, grid boxes exhibiting changes determined to be hyperfluorescence or hypofluorescence may be color coded and overlaid on a visual display of the most recent selected image. Such a visualization, may highlight the subtle changes between subsequent images in an objective and automatic manner. FIG. 8 is an example visualization in which some grid boxes within a sampled window, or macular window in this example case, of an FA image of diabetic macular disease have been highlighted to illustrate disease progression.

Although the example methods and system above are illustrated by applications to macular disease and certain imaging techniques, such as FAF, FA, and ICG, the techniques of the present disclosure may automatically measure changes in any retinal, retinal pigment epithelial, or choroidal disease, such as peripheral retinal diseases, by analyzing any suitable imagery. To illustrate this point, several example scenarios are discussed below.

Figure 9A:
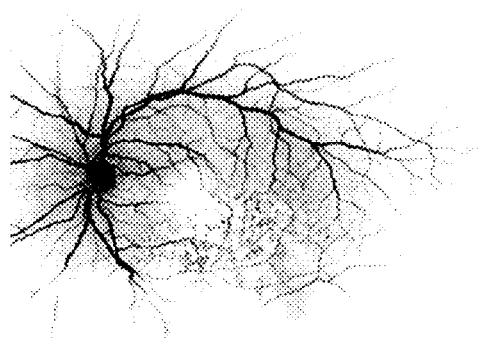
FIGS. 9A-9D illustrate example FA images analyzed to generate disease metrics such as in the method described in FIG. 7.
Figure 9B:
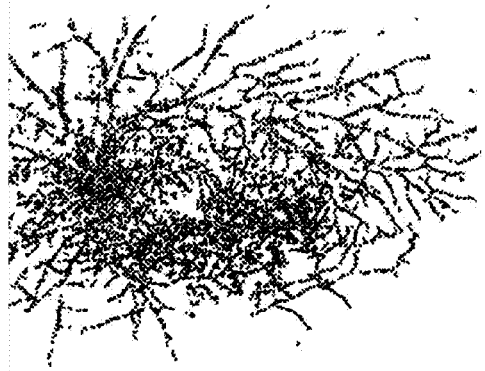
Figure 9C:
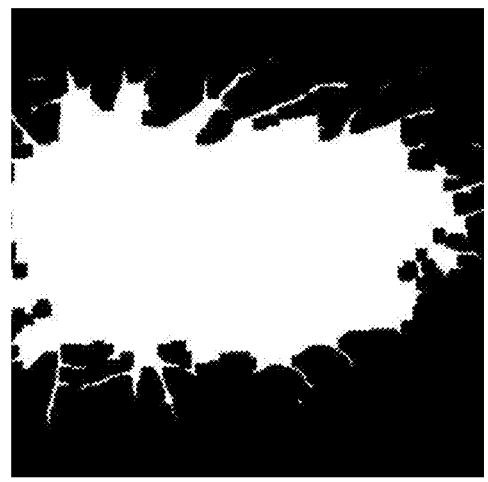
Figure 9D:
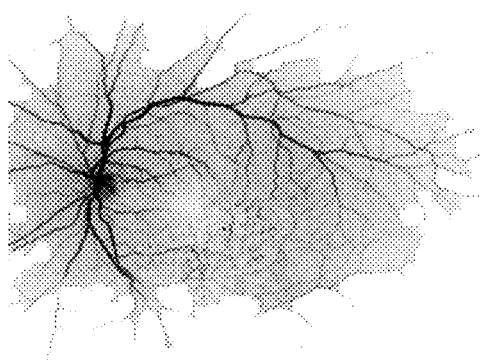

In one example scenario, a routine may automatically measure disease metrics indicating fluid leakage in or under the retina, the formation of new retinal or choroidal blood vessels, and the loss of perfusion of blood in retinal and choroidal vessels. For example, the automated measurement routine 110 may implement the method 200 and/or the method 700 to analyze FA images and output disease metrics such that a physician may: (i) diagnose areas of vascular leakage in diabetic macular edema to help target areas that should be treated with laser photocoagulation; (ii) diagnose macular lesions and characterize them as "leakage", "staining", or "window defects"; (iii) identify hypofluorescent areas of the retina that have non-perfusion or ischemia due to diseases such as diabetic retinopathy or retinal vein occlusion; (iv) identify areas of neovascularization which show leakage of fluorescein; (v) diagnose inflammatory chororioretinal diseases; (vi) detect signs of vascular or inflammatory optic nerve diseases or optic neuropathies; and (vii) detect signs of retinal or choroidal tumors. To further illustrate this scenario, FIGS. 9A-9D illustrate example FA images processed according to the techniques of the present disclosure to automatically measure perfusion of blood in retinal vessels. The example images include a captured FA image (FIG. 9A), a binary image in which vessels are detected (FIG. 9B), a closure of FIG. 9B (FIG. 9C), and an image (FIG. 9D) in which the captured image, FIG. 9A, is masked by the FIG. 9C closure. In the case of the example images FIGS. 9A-9D, the calculation of disease metrics (e.g., with method 200 and/or method 700) may include detecting the radius of the optic disc and using the estimated radius to convert the number of black pixels in the final image (FIG. 9D) to an area in $mm^2$, for example.

In another example scenario, a routine may automatically measure disease metrics indicating accumulation of fluid from retinal or choroidal vessels, the formation of new retinal or choroidal blood vessels, and the loss of perfusion of blood in choroidal vessels. For example, the automated measurement routine 110 may implement the method 200 and/or the method 700 to analyze ICG images and output disease metrics such that a physician may: (i) diagnose choroidal neovascular disease; (ii) distinguish choroidal tumors; and (iii) distinguish choroidal inflammatory diseases.

In still another example scenario, a routine may automatically measure disease metrics indicating loss (hupofluorescence) or gain (hyperfluorescence) of autofluorescence of the retina and retinal pigment epithelium. For example, the automated measurement routine 110 may implement the method 200 and/or the method 700 to analyze FAF images and output disease metrics such that a physician may: (i) detect and quantify dry age related macular degeneration progression; (ii) diagnose and quantify the progression of retinal dystrophies; (iii) diagnose and quantify changes secondary to medication or drug toxicity such as hydroxychloroquine toxicity; (iv) diagnose and quantify inflammatory diseases such as multiple evanescent white dot syndrome or retinal pigment epithelitis; and (v) diagnose choroidal melanomas and choroidal nevi.

Upon reading this disclosure, those of ordinary skill in the art will appreciate still additional alternative structural and functional designs for automatically measuring changes in retinal, retinal pigment epithelial, or choroidal disease. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

The particular features, structures, or characteristics of any specific embodiment may be combined in any suitable manner and in any suitable combination with one or more other embodiments, including the use of selected features without corresponding use of other features. In addition, many modifications may be made to adapt a particular application, situation or material to the essential scope and spirit of the present invention. It is to be understood that other variations and modifications of the embodiments of the present invention described and illustrated herein are possible in light of the teachings herein and are to be considered part of the spirit and scope of the present invention. By way of example, and not limitation, the present disclosure contemplates at least the following aspects:

1. A computer-implemented method for automatically measuring changes in retinal, retinal pigment epithelial, or choroidal disease, the method comprising:

retrieving, with one or more processors, a set of images of a fundus;

selecting, by the one or more processors, a plurality of images from the set of images, wherein the plurality of images includes images of the fundus captured at successive times;

co-registering, by the one or more processors, the plurality of images, wherein co-registering the plurality of images includes:

detecting a plurality of blood vessel locations within each of the plurality of images, correlating the detected plurality of blood vessel locations in one of the plurality of images with a plurality of blood vessel locations in the remaining plurality of images, and transforming the remaining plurality of images such that blood vessel locations in the remaining plurality of images are proximate to the detected plurality of blood vessel locations in the one of the plurality of images;

pre-processing, by the one or more processors, the plurality of images such that the quality, contrast, and gain of each of the plurality of images is made similar;

performing a comparison, by the one or more processors, of the plurality of images to determine a change in retinal, retinal pigment epithelial, or choroidal disease, wherein the change in retinal, retinal pigment epithelial, or choroidal disease is determined based on various disease metrics; and generating, by the one or more processors, an indication of the change in retinal, retinal pigment epithelial, or choroidal disease to be displayed to a user of a computing device.

2. The computer-implemented method according to aspect 1, wherein performing a comparison of the plurality of images to determine a change in retinal, retinal pigment epithelial, or choroidal disease includes:
identifying a sampled window within each of the plurality of images,
dividing the sampled window into a plurality of grid boxes,
subtracting the mean intensity within each of the grid boxes of an older image from the mean intensity within each of the corresponding grid boxes of a more recent image to produce a difference matrix,
determining a plurality of grid boxes representing an increased or decreased value of intensity as compared with a threshold value, and
calculating disease metrics based on the grid boxes representing the increased or decreased value of intensity.

3. The computer-implemented method according to either aspect 1 or aspect 2, wherein the sampled window corresponds to a macular area, a peripheral area, or an entire area of a fundus image.

4. The computer-implemented method according to any one of the preceding aspects, wherein identifying the macular window includes determining proportions of the distance between a fovea and an optic disc.

5. The computer-implemented method according to any one of the preceding aspects, wherein the locations of the fovea and the optic disc are input from a user.

6. The computer-implemented method according to any one of the preceding aspects, wherein the user inputs the locations of the fovea and the optic disc by clicking on the locations of the fovea and optic disc in a reference image.

7. The computer-implemented method according to any one of the preceding aspects, wherein the locations of the fovea and optic disc are automatically determined using computer vision algorithms executing on a reference image.

8. The computer-implemented method according to any one of the preceding aspects, wherein the reference image is one of the plurality of images with the oldest time of image capture as compared with the remaining plurality of images.

9. The computer-implemented method according to any one of the preceding aspects, wherein the disease metrics includes a mean of squared differences between values in the plurality of grid boxes representing the increased or decreased value of intensity.

10. The computer-implemented method according to any one of the preceding aspects, wherein the disease metrics include at least one of the mean of squared differences between all pixel values, only pixel values representing a change in intensity above a threshold, pixels representing only hyperfluorescence, pixels representing only hypofluorescence, or pixels in a the macular region and solid gray pixels or converting a number of pixels to a area.

11. The computer-implemented method according to any one of the preceding aspects, wherein generating an indication of the change in retinal, retinal pigment epithelial, or choroidal disease includes generating a display, on a display device of the computing device, of at least one of a three-dimensional surface plot, one or more comparison figures, one or more disease metrics, or one or more labels indicating the progressing or regressing of macular disease.

12. The computer-implemented method according to any one of the preceding aspects, wherein retrieving a set of images of a retina includes user input of the set of images.

13. The computer-implemented method according to any one of the preceding aspects, wherein retrieving a set of images of a retina includes querying a database of images based on at least one of patient name, patient identification number, or image capture date.

14. The computer-implemented method according to any one of the preceding aspects, wherein selecting a plurality of images from the set of images includes executing an image selection routine, with the one or more processors, to automatically select images according to image labels stored with the images in the image database.

15. The computer-implemented method according to any one of the preceding aspects, wherein detecting blood vessels includes applying Gaussian filtering, bottom hat filtering, and thresholding techniques.

16. The computer-implemented method according to any one of the preceding aspects, wherein correlating blood vessel locations includes executing a cross correlation algorithm to determine similar matches between blood vessel location of the plurality of images.

17. The computer-implemented method according to any one of the preceding aspects, wherein transforming the remaining plurality of images includes approximating a transformation using a Random Sample Consensus (RANSAC) algorithm.

18. The computer implemented method according to any one of the preceding aspects, wherein pre-processing the plurality of images includes at least one of removing noise with a Gaussian filter, scaling pixel intensities with a linear regression method, segmenting images, performing a histogram matching, object re-coloration, eliminating non-disease related variations with a top hat filtering method, or matching images contrasts with a gamma scaling method.

19. The computer-implemented method according to any one of the preceding aspects, wherein the set of images of the fundus includes at least one of fundus autofluorescence (FAF) images, fluorescein angiogram (FA) images, or indocyanine green (ICG) images.

20. The computer-implemented method according to any one of the preceding aspects, wherein the change in retinal, retinal pigment epithelial, or choroidal disease is related to at least one of fluid leakage in or under the retina, accumulation of fluid from retinal or choroidal vessels, formation of new retinal or choroidal blood vessels, loss of perfusion of blood in retinal vessels and choroidal vessels, or changes in autofluarescence due to retinal or retinal pigment epithelial disease and cell death.

21. A computer device for automatically measuring changes in retinal, retinal pigment epithelial, or choroidal disease, the computer device comprising:
one or more processors; and
one or more non-transitory memories coupled to the one or more processors,
wherein the one or more memories include computer executable instructions stored therein that, when executed by the one or more processors, cause the one or more processors to:
retrieve a set of images of a fundus;
select a plurality of images from the set of images, wherein the plurality of images includes images of the fundus captured at successive times;
co-register the plurality of images, wherein co-registering the plurality of images includes:
detecting a plurality of blood vessel locations within each of the plurality of images, correlating the detected plurality of blood vessel locations in one of the plurality of images with a plurality of blood vessel locations in the remaining plurality of images, and transforming the remaining plurality of images such that blood vessel locations in the remaining plurality of images are proximate to the detected plurality of blood vessel locations in the one of the plurality of images;

pre-process the plurality of images such that the quality, contrast, and gain of each of the plurality of images is made similar;

perform a comparison of the plurality of images to determine a change in retinal, retinal pigment epithelial, or choroidal disease, wherein the change in retinal, retinal pigment epithelial, or choroidal disease is determined based on various disease metrics; and generate an indication of the change in retinal, retinal pigment epithelial, or choroidal disease to be displayed to a user of a computing device.

22. The computer device according to aspect 21, wherein performing a comparison of the plurality of images to determine a change in retinal, retinal pigment epithelial, or choroidal disease includes:

identifying a sampled window within each of the plurality of images, dividing the sampled window into a plurality of grid boxes, subtracting the mean intensity within each of the grid boxes of an older image from the mean intensity within each of the corresponding grid boxes of a more recent image to produce a difference matrix, determining a plurality of grid boxes representing an increased or decreased value of intensity as compared with a threshold value, and calculating disease metrics based on the grid boxes representing the increased or decreased value of intensity.

23. The computer device according to aspect 21 or aspect 22, wherein the disease metrics include at least one of the mean of squared differences between all pixel values, only pixel values representing a change in intensity above a threshold, pixels representing only hyperfluorescence, pixels representing only hypofluorescence, or pixels in a the macular region and solid gray pixels.

We claim:

1. A computer-implemented method for automatically measuring changes in retinal disease, retinal pigment epithelial disease, or choroidal disease, the method comprising:
    retrieving, with one or more processors, a set of images of a fundus;
    selecting, by the one or more processors, a plurality of images from the set of images, wherein the plurality of images includes images of the fundus captured at successive times;
    co-registering, by the one or more processors, the plurality of images, wherein co-registering the plurality of images includes:
        detecting a plurality of blood vessel locations within each of the plurality of images by filtering each of the plurality of images to identify blood vessels,
        correlating the plurality of images by determining matches between the detected plurality of blood vessel locations in one of the plurality of images with the corresponding plurality of blood vessel locations in each remaining image in the plurality of images, and
        transforming each remaining image in the plurality of images such that blood vessel locations in the remaining image are proximate to the detected plurality of blood vessel locations in the one of the plurality of images based upon alignment of the matched blood vessel locations;
    pre-processing, by the one or more processors, the plurality of images such that the quality, contrast, and gain of each of the plurality of images is made similar;
    performing a comparison, by the one or more processors, of the plurality of co-registered and pre-processed images to determine a change in retinal disease, retinal pigment epithelial disease, or choroidal disease, by:
        identifying a sampled window representing an equivalent area of the fundus within each of the plurality of images,
        dividing the sampled window into a plurality of grid boxes, wherein each grid box is a predetermined area within the sampled window such that the plurality of grid boxes do not overlap and such that the plurality of grid boxes together cover the entire sampled window,
        subtracting the mean observed light intensity of image pixels within each of the grid boxes of an older image from the mean observed light intensity of image pixels within each of the corresponding grid boxes of a more recent image to produce a difference matrix indicating differences in mean observed light intensity for each pair of corresponding grid boxes,
        determining a plurality of changed grid boxes representing regions of the fundus having an increased or decreased value of mean observed light intensity as compared with a threshold value based upon the difference matrix, and
        calculating disease metrics based on the plurality of changed grid boxes representing the regions of the fundus having an increased or decreased value of mean observed light intensity; and
    generating, by the one or more processors, an indication of the change in retinal disease, retinal pigment epithelial disease, or choroidal disease to be displayed to a user of a computing device, the indication of the change in retinal disease including a visual display of the plurality of changed grid boxes representing the regions of the fundus having an increased or decreased value of mean observed light intensity.

2. The computer-implemented method of claim 1, wherein the sampled window corresponds to a macular area, a peripheral area, or an entire area of a fundus image.

3. The computer-implemented method of claim 2, wherein identifying the macular window includes determining proportions of the distance between a fovea and an optic disc.

4. The computer-implemented method of claim 3, wherein the locations of the fovea and the optic disc are input from a user.

5. The computer-implemented method of claim 4, wherein the user inputs the locations of the fovea and the optic disc by clicking on the locations of the fovea and optic disc in a reference image.

6. The computer-implemented method of claim 3, wherein the locations of the fovea and optic disc are automatically determined using computer vision algorithms executing on a reference image.

7. The computer-implemented method of claim 6, wherein the reference image is one of the plurality of images with the oldest time of image capture as compared with the remaining plurality of images.

8. The computer-implemented method of claim 1, wherein the disease metrics includes a mean of squared differences between values in the plurality of changed grid boxes representing regions of the fundus having an increased or decreased value of mean observed light intensity.

9. The computer-implemented method of claim 1, wherein the disease metrics include at least one of the mean of squared differences between all pixel values, only pixel values representing a change in intensity above a threshold, pixels representing only hyperfluorescence, pixels representing only hypofluorescence, or pixels in a macular region and solid gray pixels or converting a number of pixels to an area.

10. The computer-implemented method of claim 1, wherein generating an indication of the change in retinal disease, retinal pigment epithelial disease, or choroidal disease includes generating a display, on a display device of the computing device, of at least one of a three-dimensional surface plot, one or more comparison figures, one or more disease metrics, or one or more labels indicating the progressing or regressing of macular disease.

11. The computer-implemented method of claim 1, wherein retrieving a set of images of a retina includes user input of the set of images.

12. The computer-implemented method of claim 1, wherein retrieving a set of images of a retina includes querying a database of images based on at least one of patient name, patient identification number, or image capture date.

13. The computer-implemented method of claim 12, wherein selecting a plurality of images from the set of images includes executing an image selection routine, with the one or more processors, to automatically select images according to image labels stored with the images in the image database.

14. The computer-implemented method of claim 1, wherein detecting blood vessels includes applying Gaussian filtering, bottom hat filtering, and thresholding techniques.

15. The computer-implemented method of claim 1, wherein correlating the plurality of images includes executing a cross correlation algorithm to determine similar matches between blood vessel locations of a plurality of regions within each of the plurality of images.

16. The computer-implemented method of claim 1, wherein transforming the remaining plurality of images includes approximating a transformation using a Random Sample Consensus (RANSAC) algorithm.

17. The computer implemented method of claim 1, wherein pre-processing the plurality of images includes at least one of removing noise with a Gaussian filter, scaling pixel intensities with a linear regression method, segmenting images, performing a histogram matching, object re-coloration, eliminating non-disease related variations with a top hat filtering method, or matching images contrasts with a gamma scaling method.

18. The computer-implemented method of claim 1, wherein the set of images of the fundus includes at least one of fundus autofluorescence (FAF) images, fluorescein angiogram (FA) images, or indocyanine green (ICG) images.

19. The computer-implemented method of claim 1, wherein the change in retinal disease, retinal pigment epithelial disease, or choroidal disease is related to at least one of fluid leakage in or under the retina, accumulation of fluid from retinal or choroidal vessels, formation of new retinal or choroidal blood vessels, loss of perfusion of blood in retinal vessels and choroidal vessels, or changes in autofluorescence due to retinal or retinal pigment epithelial disease and cell death.

20. A computer device for automatically measuring changes in retinal disease, retinal pigment epithelial disease, or choroidal disease, the computer device comprising:
one or more processors; and
one or more non-transitory memories coupled to the one or more processors,
wherein the one or more memories include computer executable instructions stored therein that, when executed by the one or more processors, cause the one or more processors to:
retrieve a set of images of a fundus;
select a plurality of images from the set of images, wherein the plurality of images includes images of the fundus captured at successive times;
co-register the plurality of images, wherein co-registering the plurality of images includes:
detecting a plurality of blood vessel locations within each of the plurality of images by filtering each of the plurality of images to identify blood vessels,
correlating the plurality of images by determining matches between the detected plurality of blood vessel locations in one of the plurality of images with the corresponding plurality of blood vessel locations in each remaining image in the plurality of images, and
transforming each remaining image in the plurality of images such that blood vessel locations in the remaining image are proximate to the detected plurality of blood vessel locations in the one of the plurality of images based upon alignment of the matched blood vessel locations;
pre-process the plurality of images such that the quality, contrast, and gain of each of the plurality of images is made similar;
perform a comparison of the plurality of co-registered and pre-processed images to determine a change in retinal disease, retinal pigment epithelial disease, or choroidal disease, by:
identifying a sampled window representing an equivalent area of the fundus within each of the plurality of images,
dividing the sampled window into a plurality of grid boxes, wherein each grid box is a predetermined area within the sampled window such that the plurality of grid boxes do not overlap and such that the plurality of grid boxes together cover the entire sampled window,
subtracting the mean observed light intensity of image pixels within each of the grid boxes of an older image from the mean observed light intensity of image pixels within each of the corresponding grid boxes of a more recent image to produce a difference matrix indicating differences in mean observed light intensity for each pair of corresponding grid boxes,
determining a plurality of changed grid boxes representing regions of the fundus having an increased or decreased value of mean observed light intensity as compared with a threshold value based upon the difference matrix, and
calculating disease metrics based on the plurality of changed grid boxes representing the regions of the fundus having an increased or decreased value of mean observed light intensity; and
generate an indication of the change in retinal disease, retinal pigment epithelial disease, or choroidal disease to be displayed to a user of a computing device, wherein the indication of the change includes a visual display of the plurality of changed grid boxes representing the regions of the fundus having an increased or decreased value of mean observed light intensity.

21. The computer device of claim 20, wherein the disease metrics include at least one of the mean of squared differences between all pixel values, only pixel values representing a change in intensity above a threshold, pixels representing only hyperfluorescence, pixels representing only hypofluorescence, or pixels in a the macular region and solid gray pixels.

* * * * *